(12) United States Patent
Bradley et al.

(10) Patent No.: US 8,092,078 B2
(45) Date of Patent: Jan. 10, 2012

(54) MEASUREMENT OF MELTING POINTS OF MULTIPLE SAMPLES

(75) Inventors: Mark Bradley, Highfield (GB); Jean-Francois Thaburet, Yerville (FR)

(73) Assignee: University of Southampton, Southampton (GB)

( * ) Notice: Subject to any disclaimer, the term of this patent is extended or adjusted under 35 U.S.C. 154(b) by 1005 days.

(21) Appl. No.: 10/575,061

(22) PCT Filed: Oct. 11, 2004

(86) PCT No.: PCT/GB2004/004313
§ 371 (c)(1),
(2), (4) Date: Nov. 19, 2008

(87) PCT Pub. No.: WO2005/036149
PCT Pub. Date: Apr. 21, 2005

(65) Prior Publication Data
US 2009/0190626 A1 Jul. 30, 2009

(30) Foreign Application Priority Data
Oct. 9, 2003 (GB) .................................. 0323696.5

(51) Int. Cl.
*G01N 25/04* (2006.01)
*G01K 11/06* (2006.01)

(52) U.S. Cl. .................. 374/16; 374/160; 374/E11.006

(58) Field of Classification Search .................. 374/16, 374/17, 18, 19, 20, 44, 140, 160
See application file for complete search history.

(56) References Cited

U.S. PATENT DOCUMENTS

| | | | | |
|---|---|---|---|---|
| 4,927,270 A | * | 5/1990 | Bonnard | 374/16 |
| 5,092,679 A | * | 3/1992 | Brotz | 374/19 |
| 5,758,968 A | * | 6/1998 | Diebold | 374/17 |
| 6,227,702 B1 | * | 5/2001 | Yamada et al. | 374/140 |
| 6,443,616 B1 | * | 9/2002 | Brotz | 374/17 |
| 6,536,944 B1 | | 3/2003 | Archibald et al. | |
| 7,033,070 B2 | * | 4/2006 | Azami | 374/131 |
| 2003/0118078 A1 | | 6/2003 | Freitag et al. | |
| 2009/0190626 A1 | * | 7/2009 | Bradley et al. | 374/16 |
| 2011/0038392 A1 | * | 2/2011 | Ando et al. | 374/16 |

FOREIGN PATENT DOCUMENTS

DE 101 06 118 A 8/2002
EP 0 397 936 A 11/1990
(Continued)

*Primary Examiner* — Yaritza Guadalupe-McCall
(74) *Attorney, Agent, or Firm* — Merchant & Gould P.C.

(57) ABSTRACT

In a method of measuring a temperature value associated with melting, softening or decomposition of sample substances, an array of samples is deposited onto a support tray. The support tray is placed onto a heating device provided with temperature sensing means, the support tray is illuminated, and the array of samples is observed by a imaging device. WNle varying the temperature of the heating device, the image data from the imaging device is fed to an image recording device and temperature values associated with each feed of image data are also recorded. The image data is reviewed to detect changes in the image, such as image intensity, at each or selected sample locations, and the temperature of the heating device at an image change associated with a change in state of a sample is logged. Image processing software may be used to detect changes in the image, for example in the intensity of the image, at each sample location. The method may be used as a means for rapidly obtaining a melting point value for comparison of the physical characteristics of the members of a library of samples, especially polymer samples.

6 Claims, 5 Drawing Sheets

FOREIGN PATENT DOCUMENTS

| | | |
|---|---|---|
| GB | 2202941 A | 10/1988 |
| JP | 4 172240 A | 6/1992 |
| JP | 7-63664 | 3/1995 |
| JP | 10-253559 | 9/1998 |
| WO | WO 01/02089 A | 1/2001 |
| WO | WO 03/014719 A | 2/2003 |

* cited by examiner

MEASUREMENT OF MELTING POINTS OF MULTIPLE SAMPLES

BACKGROUND OF THE INVENTION

This invention is concerned with a method of measuring temperature values associated in particular with melting points, but with also decomposition points or softening points, for multiple samples of polymers or other substances, and also with apparatus for putting the method into practice. The method of the invention is especially, but not exclusively, suitable for providing melting point values for arrays of polymer samples.

Conventional methods of measuring melting points, such as observing a sample in a capillary tube or use of Differential Scanning Calorimetiy (DSC) are time consuming and involve assessing one sample at a time. Even when automated, DSC can deal with only around 12 samples per hour.

The growth of combinatorial chemistry into the polymer field, has resulted in a requirement for rapid assessment of the physical properties of new polymers. In particular there is a need for a melting point measurement system that can be adapted for the screening of multiple samples in a single operation.

SUMMARY OF THE INVENTION

The present invention is based on the finding that visual observations of a sample as it melts can detect a significant change in luminosity or reflectance of the sample consequent upon a change of phase of the sample from solid to liquid and vice versa. The change in luminosity or reflectance can be correlated with the temperature of the sample to give a reproducible melting value that can be used in rapid assessment of the physical properties if the sample. Further, using image processing technology, multiple samples can be screened for luminosity or reflectance changes in a single operation.

In its broadest aspect the present invention provides a method of measuring a temperature value associated with melting, softening or decomposition, comprising:
providing a sample support plate;
placing a plurality of discrete samples on the support plate;
varying the temperature of the support plate;
observing the sample to detect a change in luminosity or reflectance caused by a change in state of the sample;
recording the temperature of the plate associated with the change in luminosity or reflectance.

The invention has been conceived primarily as a means for rapidly obtaining a melting point value for comparison of the physical characteristics of the members of a library of samples, especially polymer samples. However, the method of the invention may also be used to record temperatures associated with other changes of state, such as softening or decomposition, which result in a change of luminosity or reflectance.

Typically the support plate is a sample tray on which the plurality of samples may be arranged in a preferably regular array.

The support tray may be placed on a heat source, such as a heating element or block with a controlled heat input so that its temperature can be varied continuously or incrementally.

The samples are preferably observed by a imaging device such as a camera, preferably a digital camera that can output digital image data. Most suitably a camera that provides a continuous output of image data is used, for example, a webcam, so that the luminosity or reflectance of the sample(s) can be continuously monitored. Most preferably the image output of the camera is monitored by image processing software arranged so that it monitors areas of the image corresponding to the location of the samples on the support plate. To ensure adequate imaging the samples are preferably illuminated by a light source so as to give constant luminosity for all experiments.

Accordingly a preferred aspect of the invention comprises forming an array of samples onto a support tray;
placing the support tray onto a heating device provided with temperature sensing means;
illuminating the support tray and observing the array of samples by a imaging device;
varying the temperature of the heating device over a temperature range from below the anticipated melting, softening or decomposition point of the samples to above the anticipated melting, softening or decomposition point of the samples;
feeding the image data from the imaging device to an image recording device during the temperature variation sequence;
recording temperature values for the temperature of the heating device associated with each feed of image data;
reviewing the image data to detect changes in the image, such as image intensity, at each or selected sample locations;
logging the temperature of the heating device recorded in respect of an image change associated with a change in state of a sample.

Most suitably, image processing software is used to detect changes in the image, for example in the intensity of the image, at each sample location. Therefore, in a preferred embodiment of the invention the heating device is provided with temperature sensing means that gives a computer readable output of the temperature of the block; the imaging device is a digital camera or webcam that feeds images to a computer loaded with the image processing software; the computer records temperature data associated with each image; and the image processing software is used to detect changes in the image intensity at each or selected sample locations; and the temperature associated with a significant change in intensity is noted.

In a preferred procedure, typically using a webcam as the digital camera, sequential images transmitted to the computer are stored in the computer memory with a temperature value transmitted from the heating block at the time of creation of the image, and after completion of the heating cycle the stored images are processed to generate data relating to the intensity of the image at selected sample locations, and the intensity data and temperature data are used to generate a plot of intensity against temperature from which melting point values for the selected samples can be assessed.

The present invention also provides apparatus for measuring melting, softening or decomposition point values comprising:
a heating device provided with temperature sensing means that gives a computer readable output of the temperature of the block;
a sample support tray that can be placed on the heating device to heat samples placed on the support tray;
a camera that can be positioned to observe samples on the support tray;
means for illuminating the samples for observation by the camera;
control means for varying the temperature of the heating block over a temperature range from below the anticipated melting, softening or decomposition point of the samples to above the anticipated melting, softening or decomposition point to the samples;

a computer to receive image data from tile digital camera and temperature data from the sensing means on the heating block;

an image processing program loaded in the computer and operable to detect changes in the image received from the digital camera, for example monitoring the intensity of the image, at each or selected sample locations;

recording means to log images at each or selected sample locations and record the temperature of the heating block associated with the images, whereby significant changes in the images can be correlated with the temperature of the heating block.

The invention is described in more detail below, by way of example only, with reference to the accompanying drawings, showing a working embodiment of an apparatus for practising the method of the invention.

DETAILED DESCRIPTION OF THE INVENTION

The present invention makes use of the property that solid substances undergoing a phase change, for example, from solid to liquid on melting, exhibit a change in luminosity or reflectance consequent on a change from a solid form which is substantially opaque to a liquid form which is substantially translucent.

In the present invention this property is used to obtain a temperature value for changes of state, such as melting point, softening point or decomposition point. The main features of the invention are: providing a sample support plate; placing sample compounds or polymers on the support plate; varying the temperature of the support plate; observing the samples to detect a change in luminosity or reflectance caused by a change in state, especially a phase change of the samples; and recording the temperature of the plate when the change in luminosity or reflectance occurs.

Figure 1:
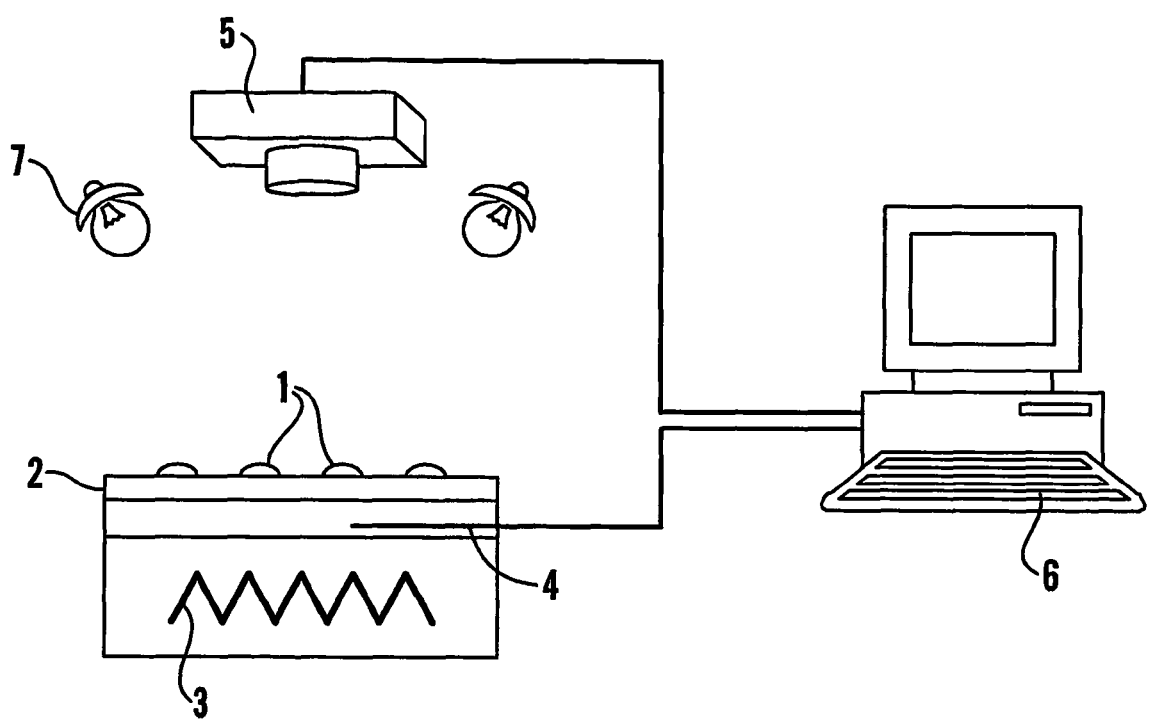
FIG. 1 is a schematic side view of apparatus in accordance with the invention.

Referring to FIG. 1 of the accompanying drawings, in a preferred embodiment of the present invention, melting point values, especially of a library of polymer samples, are measured by loading samples (1) of polymers or other substance of interest onto a support tray (2) in a regular array. The samples can be loaded as discrete solid particles or granules, or as drops of molten sample, which are allowed to solidify before testing, or as a flowable solvent-containing form, from which the solvent is evaporated before testing.

The loaded support tray (2) is placed onto a heating block (3) provided with temperature sensing means (4) that gives a computer readable output of the temperature of the heating block (3). The samples (1) are viewed by a digital camera (5), conveniently a webcam. The samples (1) are illuminated, for example by light bulbs (7), so that they are viewed under standardised conditions.

When the support tray (2) has been loaded with samples (1) and located on the heating block (3), the temperature of the heating block (3) is varied over a temperature range from below the anticipated melting point of the samples (1) to above the anticipated melting point of the samples (1). During the heating cycle, image data from the digital camera (5) is delivered to a computer (6) loaded with image processing software. The image processing software is used to monitor the intensity of the image of the loaded support tray (2) at each (or a selected) sample location. At the same time temperature data is delivered to the computer (6) from the temperature sensor (4) in the heating block (3), so that the temperature associated with, a change in the image which corresponds to the change in luminosity or reflectance expected to result from a phase change in a sample (1), can be recorded.

Apparatus suitable for measuring melting point values in accordance with the method of this invention includes:

a heating block (3) provided with temperature sensing means (4) that gives a computer readable output of the temperature of the block;

a sample support tray (2) that can be placed on the heating block (3) to heat samples (1) placed on the support tray (2);

a digital camera (5), such as a webcam, that can be positioned to observe samples (1) on the support tray (2);

light bulbs (7) or other means for illuminating the samples (1) on the support tray (2) so that the samples (1) can be viewed by the digital camera (5);

control means for varying the temperature of the heating block (3) over a temperature range from below the anticipated melting point of the samples (1) to above their anticipated melting point;

a computer (6) linked to the digital camera (5) so as to receive image data from the digital camera (5) and temperature data from the sensing means (4) on the heating block (3);

an image processing program loaded in the computer (6) and operable to detect changes in the digital camera image, for example in the intensity of the image, at each sample location;

recording means, typically in the computer memory, to record images of the sample locations and record the temperature of the heating block (3) associated with the images so that changes in image intensity can be correlated with the temperature of the sample.

The system of this invention is in principle operable to measure melting point values from both the phase change liquid-to-solid i.e. allowing the heating block to cool from a temperature above the solidification point of a sample, and for the phase change solid-to-liquid i.e. raising the temperature of the heating block from a temperature below the melting point of a sample. However the most convenient mode of operation is to make measurements by heating the sample to generate the phase change solid-to-liquid, and the invention will be described below on that basis.

The term "melting point values" is used rather than "melting point", because the aim of this invention is not so much to provide accurate melting points, which would require accurate calibration of the apparatus used, but to provide mutually consistent melting data that can be used for comparison of the physical properties of multiple samples, for example in a library of polymer samples created using combinatorial preparation techniques. The system can also be used to detect softening points or decomposition points, which will also cause a significant change in the reflectance of a sample.

As the heating block (2), a customised unit made by Ventacon (Winchester, Hants, UK) with embedded heating element has been successfully used. This may be connected to an autotune temperature controller such as Model 3300 from Cal Controls Ltd (Hitchin, Herts., UK). Suitable illumination for operation of the digital camera (5) is provided by two tubular strip lamps (284 mm length, 60 watts). The digital camera (5) may be a low-cost webcam, and preferably provides image data at a minimum of one frame per second. As a webcam, the Quickcam Model from Logitech has been successfully used.

Although the system of the invention may be used for single samples, or a small number of samples, a key aim of the invention is to provide rapid screening of multiple samples, such as a library of polymer samples obtained using combinatorial techniques.

Using the webcam mentioned above at a distance of 55 mm from the sample tray, satisfactory images for image processing have been obtained using a 60 mm×60 mm sample tray provided with 45 (an array of 9×5) sample cells of 2 mm diameter.

Figure 2:
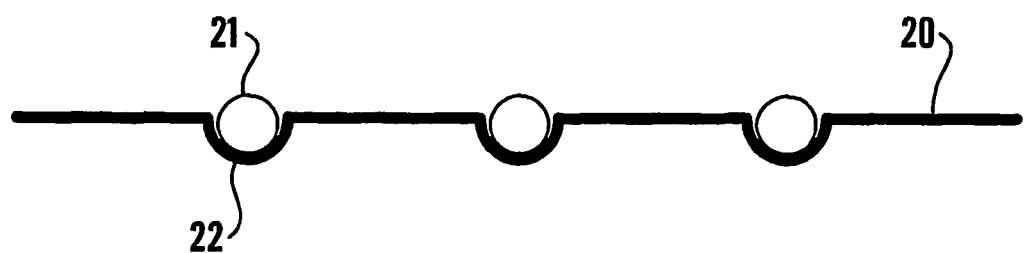
FIG. 2 is a sectional side view of a sample support tray used in the apparatus of FIG. 1.

As shown in FIG. 2, a sample support tray (20) is preferably formed with depressions (22) to act as cells to receive deposits (21) of samples of interest. The depressions may be formed for example by punching and deformation of a metal sheet or by drilling. The cells are not essential, but serve to ensure that the samples are placed in a regular array for recognition by the image processing software, and also to prevent undesirable spreading of liquefied samples. To avoid contamination of subsequent samples the support tray is preferably disposable after use. To emphasise the contrast between opaque samples and translucent liquid samples, the support tray preferably has a black finish. Then in a monochrome image, the samples appears to be "white" so that the phase change effectively is a transition from a "white" image of an opaque solid sample and a "black" image where a transparent liquid effectively has a similar intensity as the background.

Figure 3:
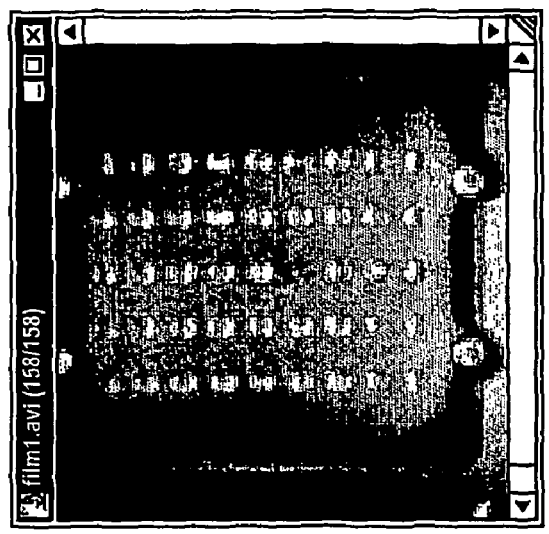
FIG. 3 shows part of a sequence of images provided by a webcam of a loaded sample support tray in the apparatus of FIG. 1 at different temperatures; (a) at 25° C., (b) at 85° C., (c) at 180° C.
Figure 3:
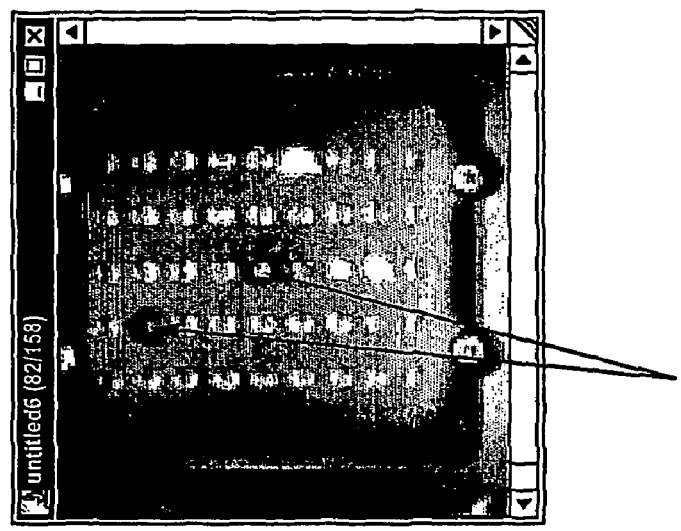
Figure 3:
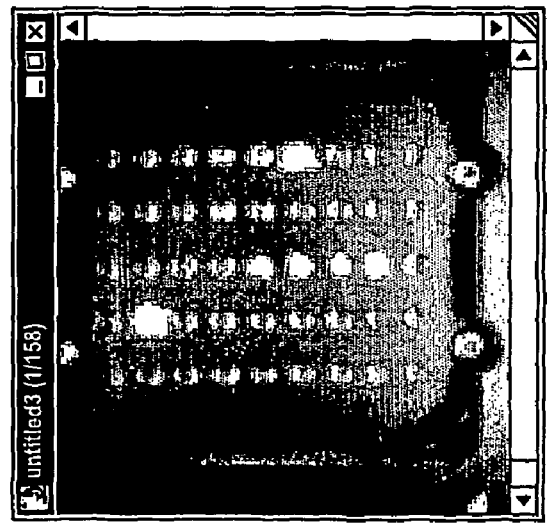

FIG. 3 shows three images from a sequence of webcam images obtained by observing samples on a black tray during a programmed rise in temperature in a procedure in accordance with this invention. In FIG. 3(a), the first frame of a sequence of 158 image frames, six samples show as a white spots on a dark background at 25° C. before melting takes place; in FIG. 3(b), frame 82 of 158, at 85° C. samples marked by arrows have melted and become colourless or transparent; in FIG. 3(c), the final frame, at 180° C. all samples have melted and become colourless. In the samples marked by arrows in FIG. 3(b), the change in image intensity from white sample to black background (seen through a colourless or transparent remelted sample) at a sample location is clearly seen.

The image processing software needs to be capable of assessing changes in selected areas of the webcam image corresponding to sample locations. The selection may be made manually using a mouse or other pointing device. The software may also be set up to automatically examine preselected areas corresponding to the fixed array of sample locations of the sample support tray. The software needs to be able to detect a change of colour intensity, which when the support tray is configured as above, is a change from white to black in the selected area of a monochrome image. The "change" event can then be recorded with an identifier of the sample location and previously-input data to uniquely identify each sample location of the array of samples under test, together with the temperature output from the sensor in the heating block at the time of the change. Depending on the frame rate of the image data output from the webcam, it may be possible for the software to produce a melting profile for each sample. The commercially available Image Plus Pro system of Media Cybernetics (Carlsbad, Calif., USA) has been used successfully in the system of this invention.

The principles of the system of this invention have been described above as effectively a "real-time" procedure, so as to explain the essential elements of the system. However, rather than detecting the image changes in real-time, it may be more convenient and efficient to record sequential images of the samples as the heating block is heated through the expected melting point range. The image data can then be analysed in respect of selected samples of interest.

Figure 4:
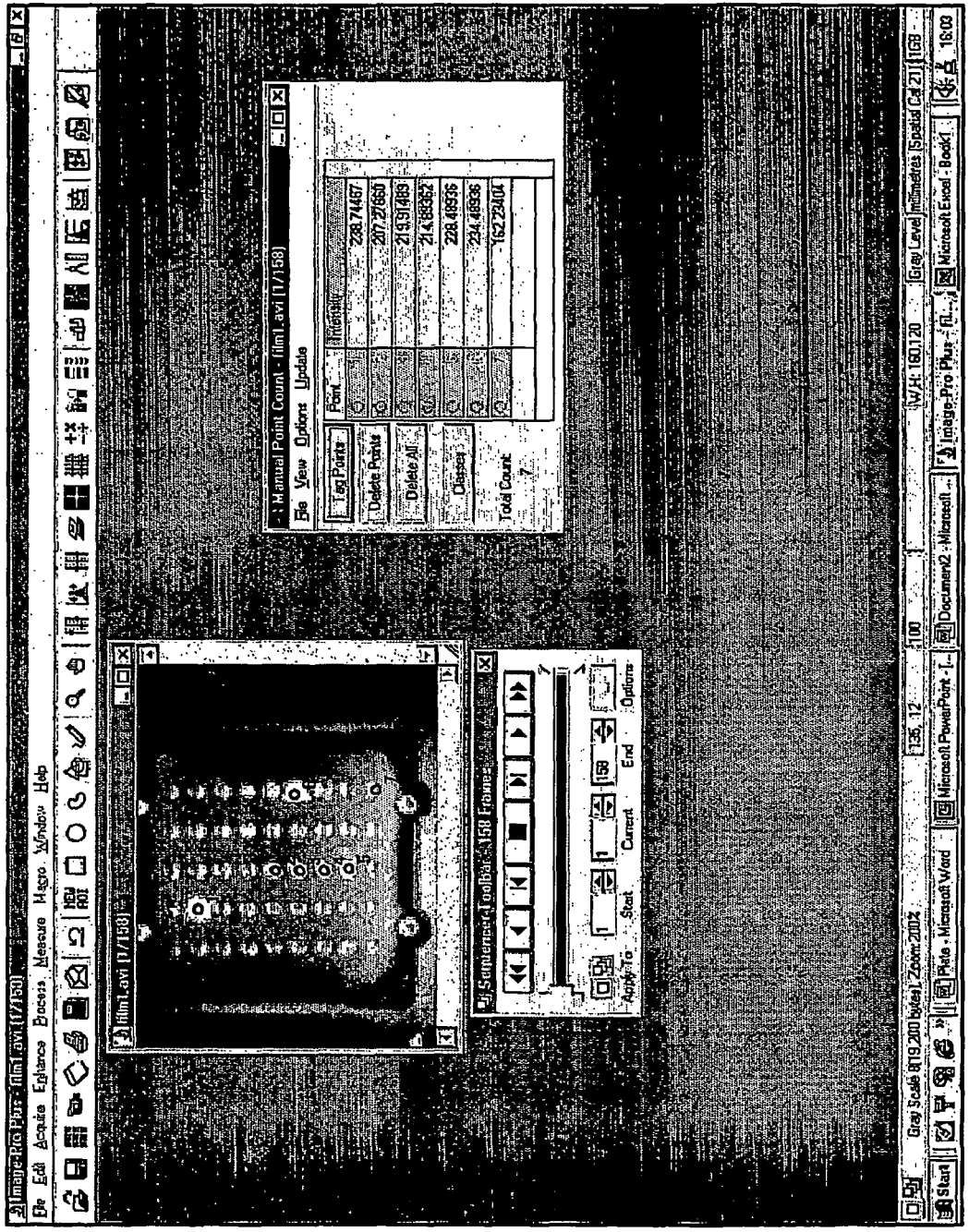
FIG. 4 is a screen shot from image processing software used for processing images of heated samples, showing the tagging of samples for study.

In a typical procedure, the heat controller is set to raise the temperature of the heating block, and the sample tray, at 10° C. per minute. The image data obtained by the webcam is stored, and then subsequently examined at one image every 5 seconds to reduce the amount of data to be processed. This means that one image is assessed for each 0.5° C. rise in temperature, which is sufficient for screening purposes. The image sequence is recorded in grey scale or in colour, where white pixels have the maximum intensity and black pixels no intensity. Selected samples are "tagged" for processing by the software in the first image from the webcam i.e. where all the samples are solid. FIG. 4 shows a screen shot from Image Plus Pro displayed during this procedure. Using the computer mouse, the six samples in the webcam image are marked with a circle on the displayed image and assigned sequential reference numbers 1 to 6 by the software. The "white" intensity of the each tagged spots are determined by the software and displayed in an adjacent window. An empty location is tagged as reference point 7 and its intensity provides a background value. The reference numbers and associated intensities can be exported to a spreadsheet to give a plot of intensity against temperature. From this plot the change of white to colourless i.e. equivalence to the black background, can be assessed, and hence the change in phase from solid to liquid detected. The melting point value can be assessed by the user of the software from the plot, or suitable threshold values can be pre-set to allow an automatic computation of the melting point value.

Figure 5:
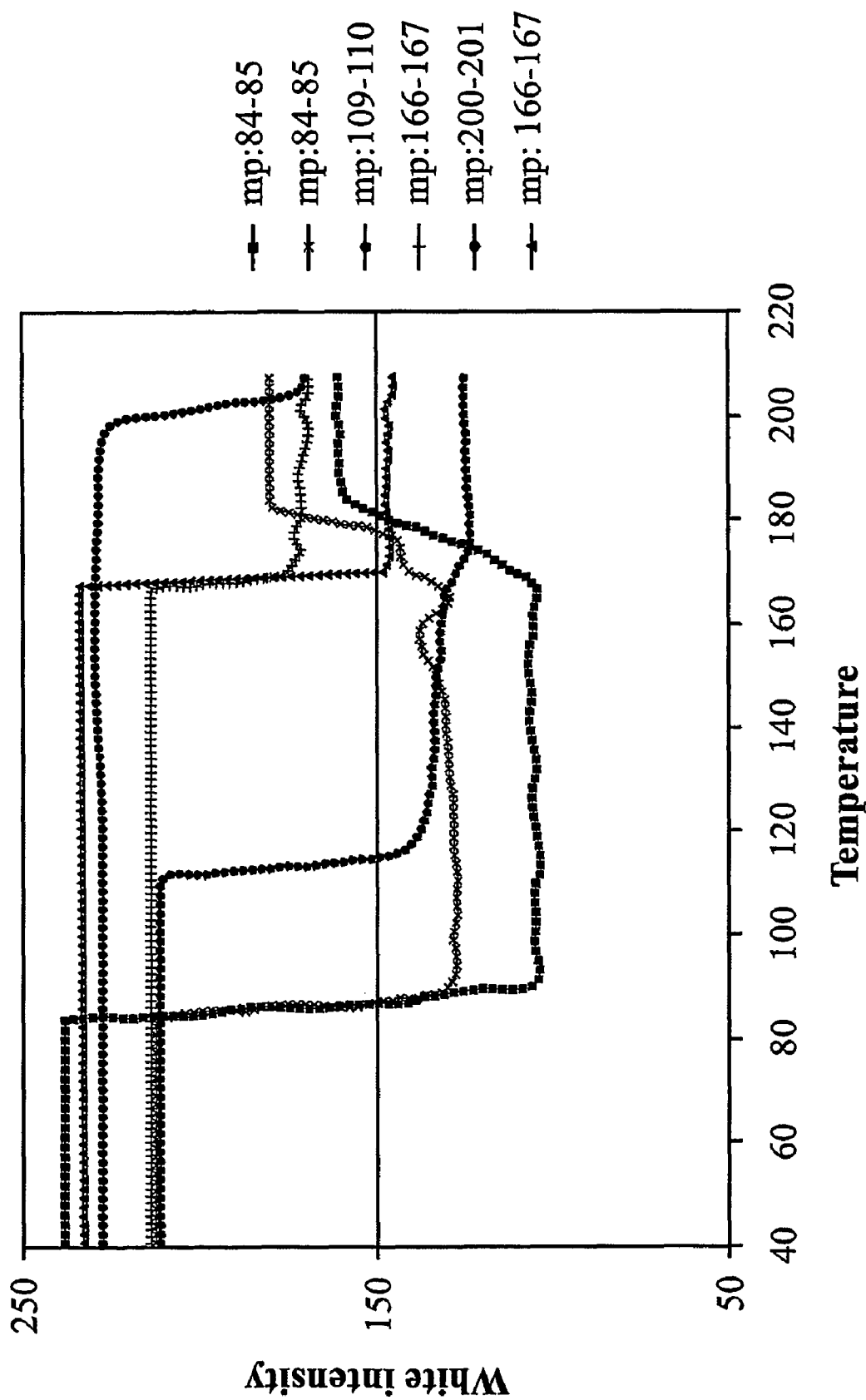
FIGS. 5 and 6 show sample plots of image intensity against temperature using values obtained by processing images of heated samples of organic compounds (FIG. 5) and polymers (FIG. 6).
Figure 6:
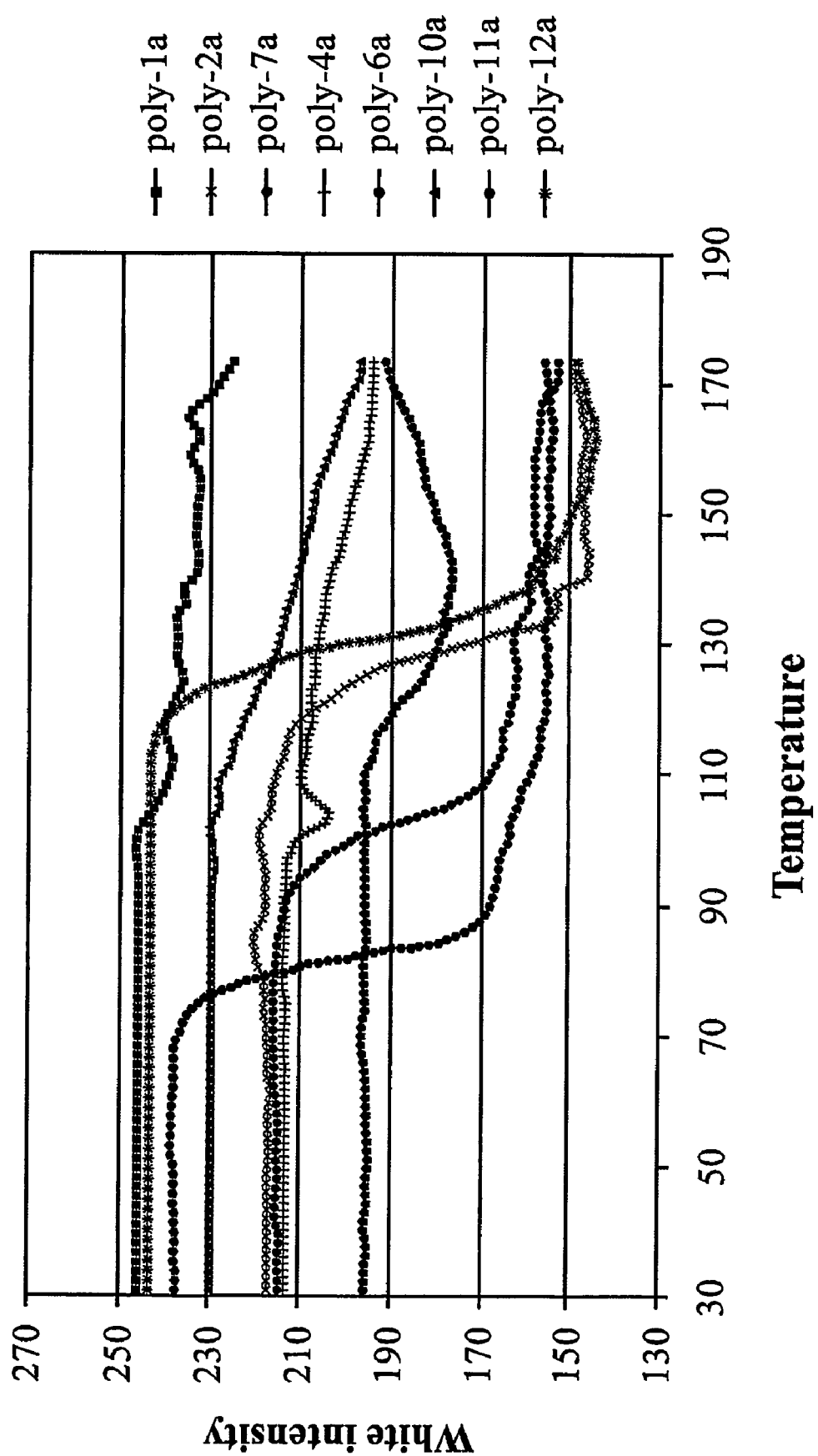

Some typical plots are shown in FIG. 5 for sample organic compounds and in FIG. 6 for sample polymers. As shown, several plots can conveniently be combined by software in a single display so that the properties of multiple samples can be compared.

INDUSTRIAL APPLICABILITY

The melting point measurement system described above is particularly suitable for the screening of multiple samples in a single operation. This allows rapid assessment of the physical properties of new polymers prepared using combinatorial chemistry techniques. As a result, new polymers having properties useful for further development for specific industrial and other uses can be rapidly identified.

The invention claimed is:

1. A method of measuring temperature value associated with melting, softening
or decomposition, comprising:
forming an array of samples on a support tray;
placing the support tray onto a heating device provided with temperature sensing means;
illuminating the support tray and the whole array of samples;
imaging the array of samples by a digital device;
varying the temperature of the heating device over a temperature range from below the anticipated melting, softening or decomposition point of the samples;
feeding an image of the whole array to a digital computer during the temperature variation sequence;

recording temperature values for the temperature of the heating device associated with each feed of image data;

reviewing the image data using image processing software loaded in the computer to detect changes in the image of the array, at each or selected sample locations;

logging the temperature of the heating device recorded in respect of an image change associated with a change in state of a sample.

2. A method according to claim 1, in which the image processing software detects changes in image intensity at sample locations.

3. A method according to claim 2 in which the heating device is provided with temperature sensing means that gives a computer readable output of the temperature of the block; the imaging device is a digital camera or webcam that feeds images to a computer loaded with the image processing software; the computer records temperature data associated with each image; and the image processing software is used to detect changes in the image intensity at each or selected sample locations; and the temperature associated with a significant change in intensity is noted.

4. A method
according to claim 3, in which sequential images transmitted to the computer are stored in the computer memory with a temperature transmitted from the heating block at the time of creation of the image, and after completion of the heating cycle the stored images are processed to generate data relating to the intensity of the image at selected sample locations, and the intensity data and temperature data are used to generate a plot of intensity against temperature from which melting point values for the selected samples can be assessed.

5. Apparatus for measuring melting point values comprising:

a heating device with temperature sensing means that gives a computer readable output of the temperature of the block;

a sample support tray that can be placed on the heating device to heat samples placed on the support tray;

a digital camera that can be positioned to image all samples on the support tray;

means for illuminating the samples for observation by the camera;

control means for varying the temperature of the heating device over a temperature range from below the anticipated melting, softening or decomposition point of the samples to above the anticipated melting, softening or decomposition points of the samples;

a computer to receive image data from the camera and temperature data from the sensing means on the heating block;

recording means to log images of the support tray and samples and record the temperature of the heating block;

an image processing program loaded in the computer and operable to review the images received from the camera, and monitor the intensity of the image at each or selected sample locations;

whereby significant changes in the images can be correlated with the temperature of the heating block.

6. Apparatus according to claim 5 in which the camera is a webcam transmitting image data to the computer during the heating sequence.

* * * * *